US010369238B2

(12) United States Patent
Xu et al.

(10) Patent No.: US 10,369,238 B2
(45) Date of Patent: Aug. 6, 2019

(54) METHOD FOR STERILIZING MEMBRANE COMPRISING GLUCOSE OXIDASE AND ASSOCIATED BIO-SENSOR

(71) Applicant: General Electric Company, Schenectady, NY (US)

(72) Inventors: Yida Xu, Shanghai (CN); Rui Chen, Niskayuna, NY (US); Lin Chen, Shanghai (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/884,310

(22) Filed: Jan. 30, 2018

(65) Prior Publication Data

US 2018/0154026 A1  Jun. 7, 2018

Related U.S. Application Data

(63) Continuation of application No. 14/402,453, filed as application No. PCT/SE2013/050612 on May 29, 2013.

(30) Foreign Application Priority Data

May 31, 2012 (CN) .......................... 2012 1 0177082

(51) Int. Cl.
*A61L 2/08* (2006.01)
*C12Q 1/00* (2006.01)
*C12Q 1/26* (2006.01)
*C12M 1/34* (2006.01)
*A61L 2/00* (2006.01)

(52) U.S. Cl.
CPC .............. *A61L 2/081* (2013.01); *C12M 41/32* (2013.01); *C12Q 1/006* (2013.01); *C12Q 1/26* (2013.01); *A61L 2/0035* (2013.01)

(58) Field of Classification Search
CPC ....................................................... A61L 2/081
See application file for complete search history.

(56) References Cited

U.S. PATENT DOCUMENTS

| 7,848,487 | B2 | 12/2010 | Miekka et al. |
| 7,875,448 | B2 | 1/2011 | Furey |
| 2002/0044884 | A1 | 4/2002 | Onodera et al. |
| 2004/0120848 | A1 | 6/2004 | Teodorczyk |
| 2005/0242479 | A1 | 11/2005 | Petisce et al. |
| 2009/0257911 | A1 | 10/2009 | Thomas et al. |
| 2010/0236923 | A1 | 9/2010 | Oviatt et al. |

FOREIGN PATENT DOCUMENTS

| DE | 4331934 | 5/1995 |
| EP | 1767225 | 3/2007 |
| WO | 9717435 | 5/1997 |
| WO | 2007022485 | 2/2007 |
| WO | 2010068587 | 6/2010 |
| WO | 2013024267 | 2/2013 |

OTHER PUBLICATIONS

Von Woedtke et al. "Sterilization of enzyme glucose sensors: problems and concepts", Biosensors & Bioelectronics, 17:373-382 (2002).
Ahmed et al. "Comparative assessment of chemical and γ-irradiation procedures for implantable glucose enzyme electrodes", Biosensors & Bioelectronics, 15:159-165 (2000).
EP Search Report issued in corresponding Application No. 13797927.4 (dated Jan. 28, 2016).
PCT/SE2013/050612 ISRWO dated Sep. 16, 2013.

*Primary Examiner* — Donald R Spamer
(74) *Attorney, Agent, or Firm* — Wood IP LLC

(57) ABSTRACT

A method for sterilizing a membrane comprising an oxidoreductase enzyme, comprises: irradiating with gamma radiation the membrane comprising an oxidoreductase enzyme soaked in an aqueous buffer solution. Associated biosensors and bioreactors are also described.

20 Claims, 2 Drawing Sheets

METHOD FOR STERILIZING MEMBRANE COMPRISING GLUCOSE OXIDASE AND ASSOCIATED BIO-SENSOR

BACKGROUND

The invention relates generally to methods for sterilizing membranes comprising oxidoreductases, such as glucose oxidase and associated biosensors.

Biosensors comprising membranes comprising glucose oxidase are used for continuous and/or automatic monitoring of glucose in bodily fluids such as in the blood stream or in interstitial fluid of certain individuals such as those with diabetes. Biosensors comprising membranes comprising the oxidoreductases glucose oxidase, lactate oxidase and glutamate oxidase are also used to automatically and/or continually detect the level of glucose, lactate and glutamate respectively in bioreactors to monitor the cell growth.

It is important that the biosensors are sterile to prevent at least potential damages from biological contaminant or pathogen (bacteria, fungi and viruses etc.) to the health and safety of the user or to the normal operation of the bioreactor.

Gamma irradiation, autoclave treatment, and ethylene oxide treatment, are some of the techniques for sterilization. However, besides eliminating/inactivating the unwanted and potentially dangerous biological contaminant or pathogen, the gamma radiation also damages the membranes comprising e.g. glucose oxidase and decreases the sensitivity of the biosensors. Therefore, methods have been developed to protect the biosensor and/or the membrane comprising glucose oxidase while sterilizing the biosensor and/or the membrane comprising glucose oxidase.

For example, US Patent Application Publication No. 2010/0293892 discloses a method of packaging an enzyme (glucose oxidase) sensor that prevents damage to the enzyme sensor and that maintains the sterility of the enzyme sensor by inflating the package with excess pressure of an inert gas or drawing a vacuum on the package before sealing the package and exposing the sealed package to radiation.

Options have also been explored to sterilize other biological materials without substantially damaging the biological materials. For instance, it is disclosed in U.S. Pat. No. 7,848,487 that urokinase, immobilized anti-insulin monoclonal antibody, and porcine heart valve cusps, after gamma irradiation in a non-aqueous environment, are able to maintain their function, but, after gamma irradiation in an aqueous environment (phosphate buffer saline solution, PBS), they lose their function significantly. In addition, US Patent Application Publication No. 2002/0044884 discloses that after gamma irradiation in a container containing a PBS solution as a filling liquid, the activity of anti-human CD4 monoclonal antibody disappears without the presence of a trisaccharide or higher saccharide having a positive charge, but maintains its function in the presence of a trisaccharide or higher saccharide having a positive charge.

It is found that by using the currently available methods, such as those proposed in the patents/patent applications mentioned above, to sterilize the biosensor and/or the membrane comprising oxidoreductases by gamma irradiation, the loss of sensitivity of the biosensor is too high in certain application environments.

Therefore, there is a need to develop a new method for sterilizing the biosensor and/or the membrane comprising oxidoreductases.

BRIEF DESCRIPTION

In one example, a method for sterilizing a membrane comprising an oxidoreductase enzyme is provided, comprising: irradiating with gamma radiation the membrane comprising an oxidoreductase enzyme soaked in an aqueous buffer solution.

In another example, a biosensor is provided. The biosensor comprises the membrane comprising an oxidoreductase enzyme sterilized using the method described above.

In yet another example, a biosensor comprising a membrane comprising an oxidoreductase enzyme is provided. The biosensor is sterilized by: irradiating with gamma radiation while the membrane comprising an oxidoreductase enzyme is soaked in an aqueous buffer solution.

The disclosure also provides a bioreactor equipped with at least one biosensor comprising a membrane comprising an oxidoreductase enzyme, which has been sterilized by irradiating with gamma radiation while the membrane comprising an oxidoreductase enzyme is soaked in an aqueous buffer solution.

These and other advantages and features will be better understood from the following detailed description of embodiments of the invention that is provided in connection with the accompanying drawings.

DETAILED DESCRIPTION

Figure 1:
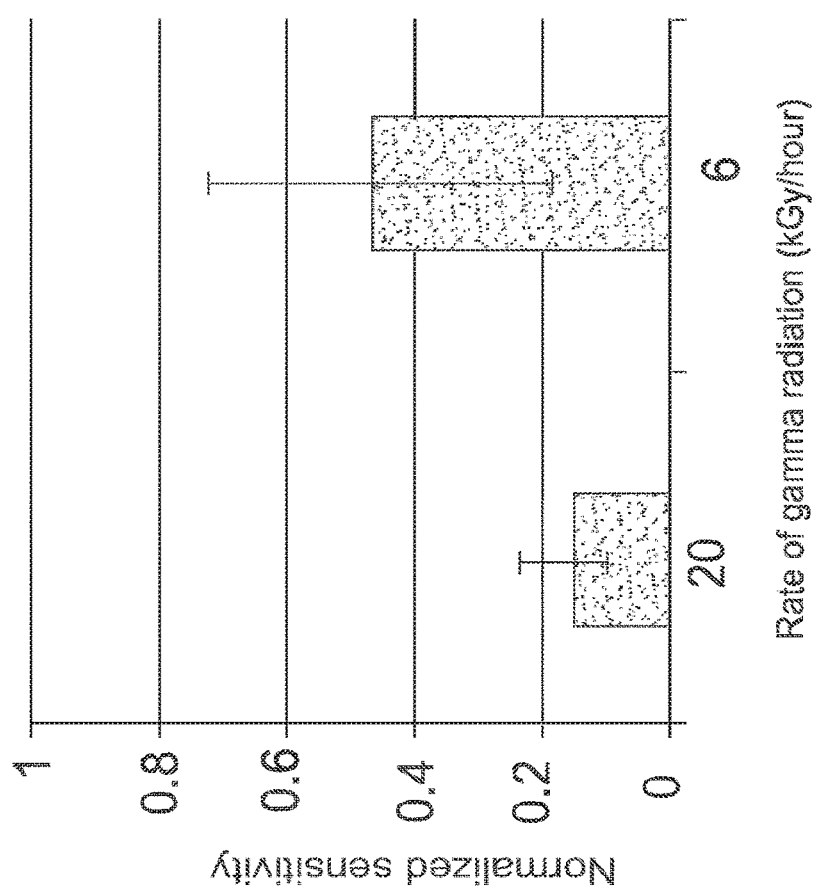
FIG. 1 is a diagram obtained in Example 1.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

Any numerical value ranges recited herein include all values from the lower value to the upper value in increments of one unit provided that there is a separation of at least 2 units between any lower value and corresponding higher value. As an example, if it is stated that the amount of a component or a value of a process variable such as, for example, temperature, pressure, rate, time and the like is, for example, from 25 to 40, it is intended that values such as 30 to 35, 26 to 39, 33 to 35, 28 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

In the following specification and claims, the singular forms "a", "an" and "the" include plural referents, unless the context clearly dictates otherwise. Moreover, the suffix "(s)" as used herein is usually intended to include both the singular and the plural of the term that it modifies, thereby including one or more of that term.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. For example, in some circumstances, an event or capacity may be expected, while in other circumstances, the event or capacity may not occur. This distinction is captured by the terms "may" and "may be".

As used herein, the terms "sterilize", "sterilizing", "sterilization" and terms of like indicate a reduction in the level of at least one active biological contaminant or pathogen found in the membrane comprising an oxidoreductase enzyme and/or the biosensor being treated according to the invention.

As used herein, the term "biological contaminant or pathogen" indicates a biological contaminant or pathogen that, upon direct or indirect contact with the membrane comprising an oxidoreductase enzyme and/or the biosensor, may have a deleterious effect on the membrane comprising an oxidoreductase enzyme or upon a recipient thereof. Such biological contaminants or pathogens include various bacteria, fungi and viruses etc.

As used herein, the term "active biological contaminant or pathogen" indicates a biological contaminant or pathogen that is capable of causing a deleterious effect, either alone or in combination with another factor, such as a second biological contaminant or pathogen or a native protein (wild-type or mutant) or antibody, in the membrane comprising an oxidoreductase enzyme and/or a recipient thereof.

The oxidoreductase enzyme may be selected from the group consisting of glucose oxidase, lactate oxidase and glutamate oxidase. Membranes comprising these enzymes can be used to determine concentrations of glucose, lactate and glutamate in e.g. bioreactors.

The aqueous buffer solution may comprise a substance buffering at a pH in the range of 6-8, such as e.g. a phosphate or a citrate. It may also comprise a non-buffering salt, such as e.g. sodium or potassium chloride. In some embodiments the aqueous buffer solution may be a phosphate buffer, such as a phosphate buffer saline (PBS) solution. The aqueous buffer solution may e.g. be substantially free from organic components such as solvents, carbohydrates etc. Such components may have a negative impact on the cultivation of cells.

In some embodiments, the recipient may be the bioreactor in which the biosensor works and the cell grows. If the biosensor is not sterilized, the "biological contaminant or pathogen" on the biosensor and/or the membrane comprising an oxidoreductase enzyme may cause the contamination of cell culture inside the bioreactor and the failure of the desired cell culture.

The membrane comprising an oxidoreductase enzyme may be any membrane that comprises an oxidoreductase enzyme, such as glucose oxidase. In some embodiments, the membrane comprising an oxidoreductase enzyme is any membrane comprising an oxidoreductase enzyme that may be used in a biosensor, e.g., for the detection of the level of glucose, lactate or glutamate. Such membranes are commercially available from, e.g., NOVA Biomedical Corporation company, Waltham, Mass. USA, YSI Incorporated and Xylem, Inc., Yellow Springs, Ohio, USA and Biology Institute of Shandong Academy of Science, Jinan, Shandong, China.

In some embodiments, the biosensor for the detection of the level of glucose, lactate or glutamate comprises a combination electrode and a membrane comprising an oxidoreductase enzyme. The combination electrode comprises two electrodes and an insulator between the electrodes. The electrodes may be made of, for example, platinum (Pt) and/or Ag/AgCl. The membrane comprising an oxidoreductase enzyme may be assembled to the biosensor after or before sterilization. In the latter case, the biosensor is sterilized by irradiating with gamma radiation while the membrane comprising an oxidoreductase enzyme thereof is soaked in an aqueous buffer, such as phosphate buffer saline solution (PBS) solution.

The invention also discloses a bioreactor equipped with at least one biosensor comprising a membrane comprising an oxidoreductase enzyme as described above. The bioreactor may e.g. comprise a presterilized plastic bag as the bioreactor vessel and the presterilized plastic bag may comprise the sterilized biosensor(s) described above. Such a bioreactor is useful for monitoring glucose, lactate, glutamate and/or other nutrients and metabolites during cell cultivation.

Gamma radiation may be produced by isotopes of cobalt or cesium. According to examples of the methods of the invention, the gamma radiation may be applied at a rate effective for the sterilization of the membrane comprising an oxidoreductase enzyme and/or the biosensor, while not causing an unacceptable level of damage to the membrane comprising an oxidoreductase enzyme. Suitable rates of gamma radiation may vary depending upon certain features of examples of the methods of the invention being employed, such as the nature and characteristics of the particular membrane comprising an oxidoreductase enzyme and/or the biosensor being irradiated, and/or the particular biological contaminants or pathogens being inactivated. Preferably, the rate of gamma radiation is constant for the duration of the sterilization procedure. When this is impractical or otherwise not desired, a variable or discontinuous irradiation may be utilized.

According to examples of the methods of the invention, the rate of gamma radiation may be optimized depending, for example, on the biological materials used. Both low ($\leq 3$ kGy/hour) and high ($>3$ kGy/hour) rates may be utilized in the methods to achieve the desired results. Although reducing the rate of gamma radiation may serve to decrease damage to the membrane comprising an oxidoreductase enzyme, it will also result in longer irradiation times normally required to achieve a particular desired total dose. A higher dose rate may therefore be preferred in certain circumstances, such as to minimize logistical issues and costs, and may be possible when used in accordance with the methods for protecting a membrane comprising an oxidoreductase enzyme from irradiation. According to one embodiment of the invention, the rate of gamma radiation is about 20 kGy/hour.

According to examples of the methods of the invention, irradiating with the gamma radiation is applied for a time period that is effective to sterilize the membrane comprising an oxidoreductase enzyme and/or the biosensor. Combined with the radiation rate, the appropriate irradiation time results in the appropriate dose of irradiation being applied to the membrane comprising an oxidoreductase enzyme and/or the biosensor. Suitable irradiation times may vary depending upon the particular rate of radiation involved and/or the nature and characteristics of the particular membrane comprising an oxidoreductase enzyme and/or the biosensor being irradiated.

According to examples of the methods of the invention, the time and rate of irradiating with gamma radiation will depend on the total dose effective to sterilize the membrane comprising an oxidoreductase enzyme and/or the biosensor, while not producing an unacceptable level of damage to that membrane comprising an oxidoreductase enzyme. Suitable total doses of gamma radiation may vary depending upon certain features of examples of the methods of the invention being employed, such as the nature and characteristics of the particular membrane comprising an oxidoreductase enzyme and/or the biosensor being irradiated, the particular form of gamma radiation involved and/or the particular biological contaminants or pathogens being inactivated. In one example, the total dose of gamma radiation is at least about 25 kGy, and in other examples it may be in a range of from about 25 kGy to about 40 kGy.

According to examples of the methods of the invention, irradiating with gamma radiation may occur at any temperature that is not deleterious to the membrane comprising an oxidoreductase enzyme and/or the biosensor being sterilized. The irradiation occurs at any temperature that does not substantially damage the membrane comprising glucose oxidase and/or the biosensor.

In some embodiments, irradiating with gamma radiation is at an ambient temperature. According to another embodiment, the irradiation is at a reduced temperature, e.g., a temperature below ambient temperature, such as 0° C., −20° C., −40° C., −60° C., −78° C. or −196° C. According to another embodiment, the irradiation is at elevated temperature, e.g., a temperature above ambient temperature, such as 37° C., 60° C., 72° C. or 80° C.

In certain embodiments, the temperature at which irradiation is performed may be found to lie within a range, rather than at a specific point.

According to examples of the methods of the invention, the irradiation may occur at any pressure which is not deleterious to the membrane comprising an oxidoreductase enzyme and/or the biosensor being sterilized. According to one embodiment, the irradiation is at an ambient pressure.

PBS solution is a water-based salt solution comprising sodium phosphate, and/or, in some formulations, sodium chloride, potassium chloride and potassium phosphate. The sodium/potassium phosphate may be sodium/potassium phosphate dibasic and sodium/potassium acid phosphate. Some formulations of PBS buffer contain calcium or magnesium. In some embodiments, the pH of the PBS solution is about 7. An exemplary composition of a PBS solution having a pH of 7.4 is listed in table 1 below.

TABLE 1

| Salt | Concentration (mmol/L) | Concentration (g/L) |
|---|---|---|
| NaCl | 137 | 8.01 |
| KCl | 2.7 | 0.20 |
| $Na_2HPO_4 \cdot 2H_2O$ | 10 | 1.78 |
| $KH_2PO_4$ | 2.0 | 0.27 |

In some embodiments, a PBS solution may be prepared from formulated PBS powders by dissolution in a specified quantity of deionized water, such as 100, 200, 500 or 1000 mL. In some embodiments, the PBS powders may have exemplary compositions as listed in table 2 below.

TABLE 2

| Chemical Name | % Weight |
|---|---|
| Sodium phosphate dibasic | 50-55 |
| Sodium acid phosphate | 10-15 |
| Sodium chloride | 16-22 |
| Glycine, N,N'-ethanediybis (N-carboxymethyl) dipotassium salt, dihydrate | <10 |

TABLE 2-continued

| Chemical Name | % Weight |
|---|---|
| Sodium benzoate | <10 |
| Gentamicin sulfate (salt) | <1 |

As can be seen from the following examples, the sensitivity of the biosensor comprising the membrane comprising an oxidoreductase enzyme such as glucose oxidase, that is protected by being soaked in a phosphate buffer saline solution while being irradiated with gamma radiation, is higher than the sensitivity of the biosensor comprising the membrane comprising an oxidoreductase enzyme without the protection while being irradiated with gamma radiation.

EXAMPLES

The following examples are included to provide additional guidance to those of ordinary skill in the art in practicing the claimed invention. These examples do not limit the invention of the appended claims.

The membranes comprising glucose oxidase and dry-sealed in an aluminum foil pouch were obtained from NOVA Biomedical Corporation company, Waltham, Mass., USA and were stored at 4° C. before use. In the following examples, unless otherwise noted, all irradiation was accomplished using a $^{60}Co$ source at an ambient temperature and pressure, and dosages of gamma radiations were in a range of from about 25 kGy to about 40 kGy. The pH of the PBS solution was about 7.

Example 1

Four membranes comprising glucose oxidase were sterilized by being irradiated with gamma radiation in the aluminum foil pouches. The rate of gamma radiation for two of the four membranes comprising glucose oxidase was 6 kGy/hour. The rate of gamma radiation for the other two of the four membranes comprising glucose oxidase was 20 kGy/hour.

Each of the four membranes comprising glucose oxidase was assembled to a combination electrode comprising a Pt working electrode, an Ag/AgCl reference/counter electrode and an insulator between the Pt working electrode and the Ag/AgCl reference/counter electrode to obtain a biosensor.

Each of the biosensors was soaked in a PBS buffer comprising glucose, and connected to a potentiostat via cables. A voltage of 0.6 V was applied to the biosensor using the potentiostat.

The concentration of the glucose in the PBS buffer was increased step by step and the current was read from the potentiostat at each concentration. A two dimensional figure was made using the concentration of the glucose as the horizontal axis and the corresponding current as the vertical axis. The slope of the figure of the current vs. the concentration of glucose was obtained and used to stand for the sensitivity of the biosensor.

The sensitivities obtained above were respectively divided by the sensitivities of biosensors comprising membranes comprising glucose oxidase without gamma irradiation to yield values of normalized sensitivities shown in FIG. 1. It can be seen from FIG. 1 that about 50% of the sensitivity remained after 6 kGy/hour gamma irradiation, but only less than 20% of the sensitivity remained after 20 kGy/hour gamma irradiation.

Example 2

A pack of PBS buffer powders for a bioanalyzer (SBA-40C, Biology Institute of Shandong, Academy of Science, Jinan, Shandong, China) was obtained from the Biology Institute of Shandong Academy of Science, Shandong, China and was dissolved using 500 ml deionized water to obtain the PBS solution.

Two membranes comprising glucose oxidase were irradiated with gamma radiation in the aluminum foil pouches. Two membranes comprising glucose oxidase were irradiated with gamma radiation while being soaked in 1-2 drops of the PBS solution in a small plastic container. The rate of gamma radiation of each glucose oxidase membrane was 20 kGy/hour.

Figure 2:
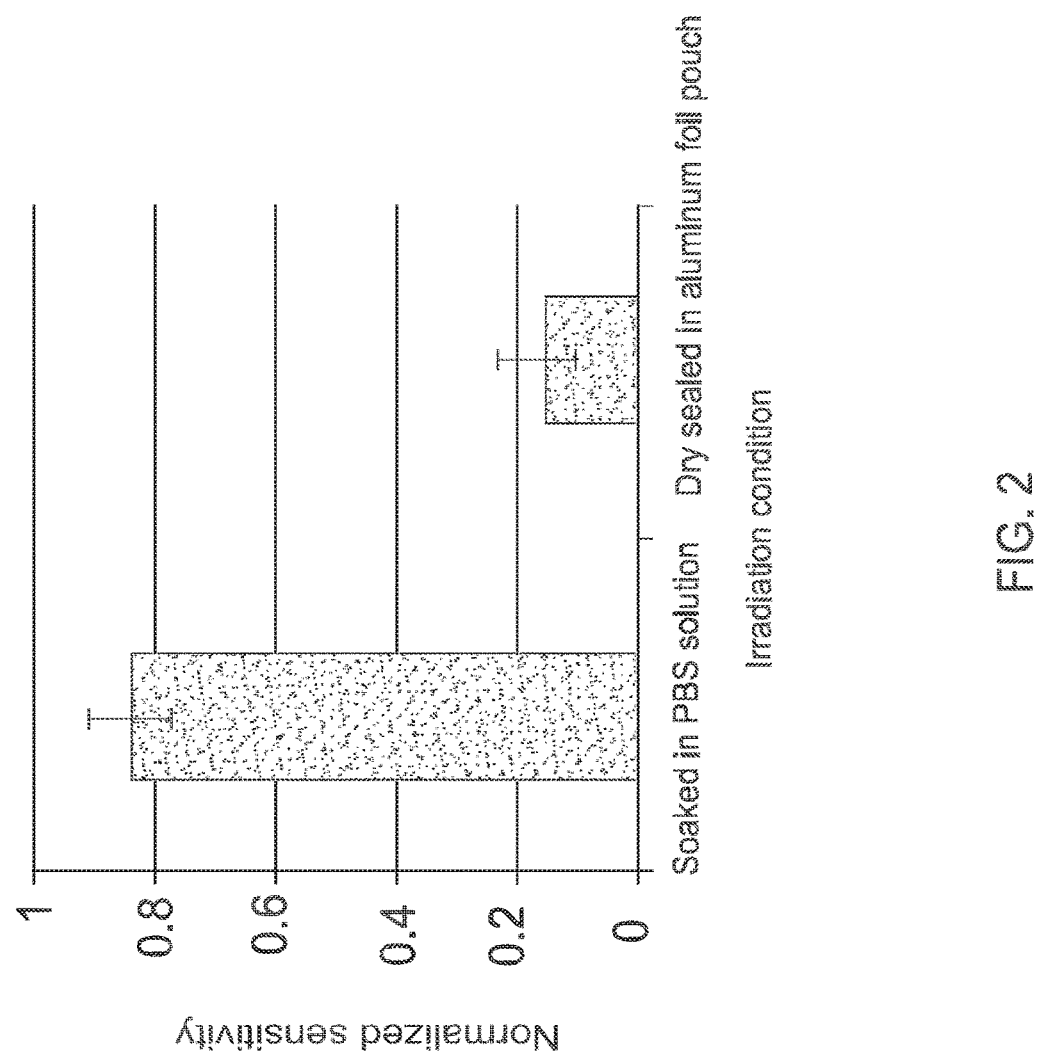
FIG. 2 is a diagram obtained in Example 2.

The sensitivities of the biosensors comprising the above four membranes were obtained in the same ways as in example 1 above and were respectively divided by the sensitivities of biosensors comprising membranes comprising glucose oxidase without gamma irradiation to yield values of normalized sensitivities shown in FIG. 2.

It can be seen from FIG. 2 that about 80% of the sensitivity remained after gamma irradiation while the membranes comprising glucose oxidase were soaked in PBS buffer and only less than 20% of the sensitivity remained after gamma irradiation while the membranes comprising glucose oxidase those were merely dry-sealed in the aluminum foil pouches.

While the methods have been illustrated and described in typical embodiments, these are not intended to be limited to the details shown, since various modifications and substitutions may be made without departing in any way from the spirit of the disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method for sterilizing a membrane comprising an oxidoreductase enzyme, the method comprising:
    irradiating with gamma radiation the membrane comprising the oxidoreductase enzyme soaked in a phosphate buffer saline (PBS) buffer solution,
    wherein the PBS buffer consists essentially of sodium phosphate dibasic, sodium acid phosphate, sodium chloride, glycine, N, N'-ethanediybis (N-carboxymethyl) dipotassium, sodium benzoate, and gentamicin sulphate in water.
2. The method of claim 1, wherein the oxidoreductase enzyme is selected from the group consisting of glucose oxidase, lactate oxidase and glutamate oxidase.
3. The method of claim 2, wherein the oxidoreductase enzyme is glucose oxidase.
4. The method of claim 1, wherein the wherein the gamma radiation is conducted at a rate of more than 3 kGy/hour and a dose of at least 25 kGy.
5. The method of claim 1, wherein the aqueous buffer solution is substantially free from organic components.
6. A method for sterilizing a membrane comprising glucose oxidase, the method comprising:
    making a phosphate buffer saline (PBS) solution by dissolving a PBS buffer powder in water,
    wherein the PBS buffer powder consists essentially of 50-55% wt sodium phosphate dibasic, 10-15% wt sodium acid phosphate, 16-22% wt sodium chloride, less than 10% wt glycine and N, N'-ethanediylbis (N-carboxymethyl) dipotassium, less than 10% wt sodium benzoate, and less than 1% wt gentamicin sulphate, and
    irradiating with gamma radiation the membrane comprising glucose oxidase soaked in a phosphate buffer saline (PBS) solution,
    wherein the gamma radiation is carried out in a range of from about 25 kGy to about 40 kGy at rate of about 20 kGy/hour.
7. The method of claim 1, wherein a dose of the gamma radiation is in a range of from about 25 kGy to about 40 kGy.
8. The method of claim 1, wherein a rate of the gamma radiation is about 20 kGy/hour.
9. The method of claim 1, wherein the membrane is in a plastic container.
10. The method of claim 1, wherein the membrane is in a biosensor.
11. The method of claim 10, wherein the biosensor comprises a Pt electrode and an Ag/AgCl electrode.
12. The method of claim 6, wherein the biosensor comprises a Pt electrode and an Ag/AgCl electrode.
13. A biosensor comprising the membrane sterilized using the method of claim 1.
14. The biosensor of claim 13, wherein the membrane comprises glucose oxidase and the sensitivity of the biosensor to glucose is about 80% of the sensitivity of a biosensor comprising a membrane comprising glucose oxidase without sterilization to glucose.
15. The biosensor of claim 13, comprising a Pt electrode and an Ag/AgCl electrode.
16. A bioreactor comprising the biosensor of claim 13.
17. A biosensor comprising a sterilized membrane that comprises glucose oxidase, wherein the membrane is sterilized by: irradiating with gamma radiation while the membrane comprising glucose oxidase is soaked in a phosphate buffer saline (PBS) solution,
    wherein the PBS buffer is made by dissolving a PBS powder in water, wherein the PBS buffer powder consists essentially of 50-55% wt sodium phosphate dibasic, 10-15% wt sodium acid phosphate, 16-22% wt sodium chloride, less than 10% wt glycine and N, N'-ethanediylbis (N-carboxymethyl) dipotassium, less than 10% wt sodium benzoate, and less than 1% wt gentamicin sulphate, and
    wherein the gamma radiation is carried out in a range of from about 25 kGy to about 40 kGy at rate of about 20 kGy/hour.
18. The biosensor of claim 17, wherein the biosensor comprises a Pt electrode and an Ag/AgCl electrode.
19. The biosensor of claim 17, wherein the sensitivity of the sterilized biosensor to glucose is about 80% of the sensitivity of a biosensor prior to sterilization.
20. A bioreactor comprising the biosensor of claim 17.

* * * * *